United States Patent
Kirchhofer et al.

(10) Patent No.: US 7,699,816 B2
(45) Date of Patent: Apr. 20, 2010

(54) INJECTION DEVICE WITH PRIMING STROKE

(75) Inventors: Fritz Kirchhofer, Sumiswald (CH); Eugen Bucher, Muehlethurnen (CH)

(73) Assignee: TecPharma Licensing AG, Burgdorf (CH)

( * ) Notice: Subject to any disclaimer, the term of this patent is extended or adjusted under 35 U.S.C. 154(b) by 1079 days.

(21) Appl. No.: 11/106,024

(22) Filed: Apr. 14, 2005

(65) Prior Publication Data
US 2005/0222540 A1    Oct. 6, 2005

Related U.S. Application Data

(63) Continuation of application No. PCT/CH03/00663, filed on Oct. 9, 2003.

(30) Foreign Application Priority Data

Oct. 15, 2002   (DE) .............................. 102 48 061

(51) Int. Cl.
*A61M 5/315* (2006.01)

(52) U.S. Cl. ............. 604/218; 604/187; 604/207; 604/246

(58) Field of Classification Search ............... 604/187, 604/218, 246, 207
See application file for complete search history.

(56) References Cited

U.S. PATENT DOCUMENTS

| | | | |
|---|---|---|---|
| 4,883,472 A | * | 11/1989 | Michel ................ 604/208 |
| 5,112,317 A | | 5/1992 | Michel |
| 5,391,157 A | | 2/1995 | Harris et al. |
| 6,048,336 A | | 4/2000 | Gabriel |

FOREIGN PATENT DOCUMENTS

| | | |
|---|---|---|
| DE | 38 14023 A1 | 1/1989 |
| DE | 39 00 926 A1 | 8/1989 |
| DE | 44 28 467 A1 | 2/1996 |
| DE | 295 13 214 U1 | 1/1997 |
| DE | 694 21 928 T2 | 3/2000 |
| WO | WO 90/09202 | 8/1990 |
| WO | WO 94/26331 * | 11/1994 |
| WO | WO 03/020347 A2 | 3/2003 |

* cited by examiner

*Primary Examiner*—Nicholas D Lucchesi
*Assistant Examiner*—Victoria P Campbell
(74) *Attorney, Agent, or Firm*—Dorsey & Whitney LLP; David E. Bruhn, Esq.

(57) ABSTRACT

A device for administering metered doses of an injectable product, including a housing, a drive member with a plunger, a drive button which, when displaced, moves the drive member relative to the housing, and at least one delaying member, which can be moved from a first position into a second position by displacing the drive button relative to the drive member in the longitudinal direction of the device, the drive member remaining stationary relative to the housing, whereby the at least one delaying member establishes a contact with the drive member in the first or second position so that when the drive button is displaced, the drive member can be moved in the forward direction before or after the at least one delaying member is moved relative to the drive member.

16 Claims, 5 Drawing Sheets

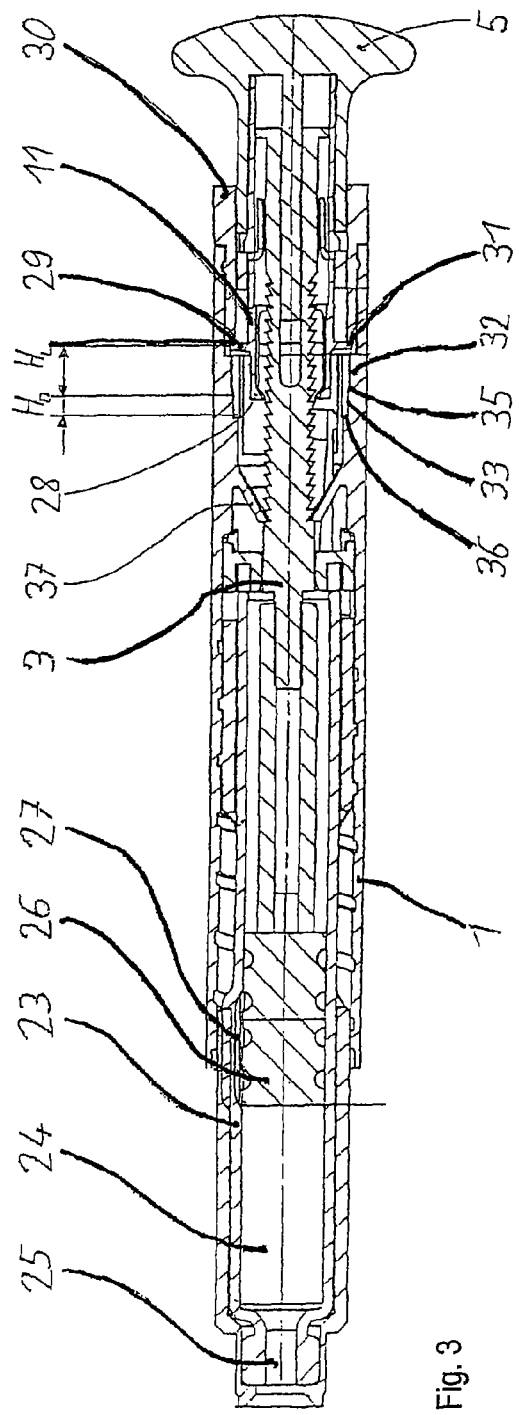
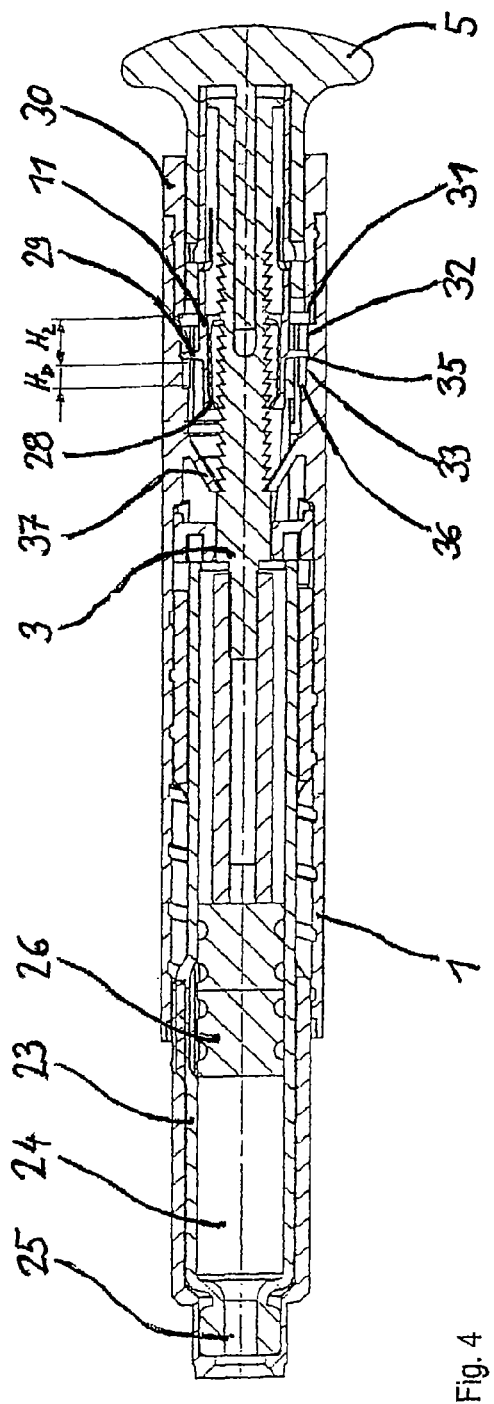
Fig. 3
Fig. 4

INJECTION DEVICE WITH PRIMING STROKE

CROSS-REFERENCE TO RELATED APPLICATIONS

This application is a continuation of International Application No. PCT/CH2003/00663, filed on Oct. 9, 2003, which claims priority to German Application No. 102 48 061.3, filed on Oct. 15, 2002, the contents of which are incorporated in their entirety by reference herein.

BACKGROUND

The invention relates to devices and methods for administering metered amounts or doses of an injectable product, in particular to devices and methods involving the type of injection devices known as injection pens for, e.g., administering insulin.

A device of the type to which the invention relates is known from the specification of document WO 97/36626. The device has a housing incorporating a reservoir for the product. A plunger is accommodated in the reservoir, which forces the product out of the reservoir through an outlet of the reservoir when pushed in a forward direction. A toothed rack serves as a plunger rod and pushes the plunger in the forward direction. Also disposed in the housing is a drive member which is slidable relative to the housing in the forward direction and in reverse, which drives the toothed rack with it when pushed in the forward direction. To this end, the drive member has drivers which engage in rows of teeth of the toothed rack. In order to set the quantity of product to be administered with one stroke, i.e., by operating a dose metering unit, the drive member is manually pulled back from a forward position in the direction opposite the forward direction by a set length defining the dose. As this happens, the drivers of the drive member slide across the teeth of the rows of teeth of the toothed rack and elastically give way. The toothed rack is prevented from being pushed back by locking means which are secured so as to prevent any sliding relative to the housing. The locking means co-operate with one of the rows of teeth of the toothed rack so that the locking means prevent the toothed rack from sliding in the direction opposite the forward direction. They allow the toothed rack to slide in the forward direction due to elastic flexibility. When the drive button is operated, the set path length defining the dose is travelled by the toothed rack and plunger due to the drive member so that the set dose is dispensed through the outlet of the reservoir.

The specification of EP 0498737 discloses a dose metering unit for an injection device, incorporating a mechanism for setting the dose and administering the product. The mechanism moves a sleeve between two settings. In the position intended as a means of setting the dose, the length by which a plunger rod will be displaced is set and hence also the dose. Accordingly, locating jaws connected to a drive member are not engaged with the plunger rod. When the sleeve is turned into the second position, the injection device is in an injection-ready state. Accordingly, the jaws engage between teeth of a row of teeth of the plunger rod, pushing the drive member. As the drive member is pushed in, the jaws engage directly in the row of teeth. The injection device also has a return lock for the plunger rod. To this end, two claws are provided in the interior of the injection device, which do not locate in the plunger rod in the released state. In this state, the plunger rod can be displaced backwards and forwards. When an ampoule is turned in the injection device, an edge provided within a housing sleeve for the ampoule opposes the claws and pushes their teeth into the row of teeth. However, because of the layout of the teeth of the toothed rack and the claws, the locating action is such that the plunger rod is able to move in the forward direction but not in an opposite direction.

U.S. Pat. No. 6,228,067 describes an injection device which also has a dose metering and drive unit. When two housing regions are turned towards one another, an axial displacement of a metering element is triggered in one of the housing parts, thereby enabling a specific dose to be set. In this instance, the drive unit is initially engaged with a toothed rack, which pushes the plunger forward to dispense the dose. When an operating element is pulled back, the toothed rack is pulled back in the direction opposite the forward direction but the plunger remains in its position because locating projections engage between teeth of a row of teeth of the toothed rack. The locating projections are disposed on an extension of an operating button and when located are biased. When the operating button is pulled out, the plunger rod is displaced in the direction opposite the forward direction until cams provided on the extensions opposite the projections locate in recesses of the housing internal face due to the biasing action. As a result, the projections are pulled out of the intermediate spaces of the row of teeth of the toothed rack, so that they are released. A spring moves them in the forward direction until they sit against the plunger. To administer an injection, the operating button is moved in the forward direction, causing the cams of the extensions to be forced out of the recesses in the internal face of the housing, thereby pushing the projections between the teeth of the row of teeth so that the operating button engages with the plunger rod again.

The path length or travel defining the dose in the injection devices known from the prior art is generally very short, which means that the operating button also has to be moved by this short path length in order to administer an injection. As soon as the operating button is moved in the forward direction, the different drive mechanisms engage on the plunger rod and move it in the forward direction, thereby dispensing the desired dose. Due to the fact that there is little room left for the operating button to move when administering an injection, it is often difficult for the user to see and/or determine in what position or what state the injection device is at any one time. To ensure that the entire path length determining the dose is covered, it is often necessary to exert an unnecessarily high force on the operating button or on the entire injection device. This can lead to uncertainties in terms of guiding the device, and/or may lead to excessive wear of the material.

SUMMARY

Accordingly, objectives of the present invention are to provide a device for administering metered doses of an injectable product which is simple to use and which has a reliable guide system when being used. Another objective is to provide a device that substantially guarantees that a desired dose is reliably administered. A further objective is to provide injection or administering devices wherein control of the devices is perceptibly and visibly improved, especially if the path length determining the dose is short.

These objectives are addressed by an administering or injection device in accordance with one embodiment of the present invention, wherein the device comprises a housing, a drive member with a plunger, a drive button which, when displaced, moves the drive member relative to the housing, and at least one delaying member, moveable relative to the drive member and from a first position into a second position by displacing the drive button relative to the drive member in the longitudinal direction of the device, the drive member remaining stationary relative to the housing, whereby the at least one delaying member establishes a contact with the drive member in the first or second position so that when the drive button is displaced the drive member can be moved in the forward direction before or after the at least one delaying member is moved relative to the drive member.

In one embodiment, the device has a housing incorporating a reservoir for a substance to be injected, at least one drive member with a plunger which forces product out of the reservoir through an outlet when moved in a forward direction, and a drive button which, when displaced, moves the drive member relative to the housing, and wherein the device comprises at least one delaying member moveable from a first position into a second position at a distance apart from the first position by displacing the drive button relative to the drive member in the longitudinal direction of the device, whereby the drive member remains stationary relative to the housing and the at least one delaying member establishes contact with the drive member in the first or second position so that when the drive button is displaced, the drive member is moveable in the forward direction before or after the at least one delaying member is moved relative to the drive member.

An administering device in accordance with the present invention has a housing incorporating a reservoir for a product to be injected. This being the case, the reservoir may be refillable or may be provided in the form of an inter-changeable ampoule, for example. When pushed in a forward direction, a plunger forces the product out of the reservoir through an outlet. At least one drive member is used to slide the plunger, for example a plunger rod, preferably a toothed rack. It would also be possible to use several drive members, such as a toothed rack and a member which engages in the toothed rack in order to effect a forward movement. The plunger rod is pushed in the forward direction by the user, by operating a drive button. The drive button preferably projects axially out from the end of the housing lying opposite the product outlet. The drive button may co-operate directly with the plunger rod or may act on another drive member which in turn makes contact with the plunger rod.

In accordance with the present invention, the administering device has at least one delaying member, which is slidable from a first position into a second position at a distance apart from the first position, relative to the drive member, i.e. to the plunger rod, by operating the drive button in the longitudinal direction of the device. The plunger rod, and hence the plunger acting on the product in the reservoir, remains stationary when the delaying member is moved from the first into the second position relative to the housing or reservoir. The displacement of the delaying member from the first to the second position causes the drive button to travel a priming stroke length because in spite of being operated, no product is administered. The delaying member is preferably fixedly joined to the drive button or is designed as an integral part of it. This being the case, it may enclose the drive member or plunger rod in a sleeve-type arrangement or may simply be designed as a beam-type extension of the drive button. The first and second positions of the delaying member are preferably fixed positions which can be released in such a way that these specific positions remain unchanged unless acted on by a force, i.e. unless the drive button is operated. The delaying member can not be released from these fixed positions and moved relative to the plunger rod or drive member until a force is applied, i.e. by operating the drive button. If the dose is to be administered prior to overcoming the priming stroke length, the contact between the delaying member and drive member in the first position is so firm that the plunger rod is pushed across the dose displacement length. It then hits a stop, for example, which stops its sliding motion and when the drive button is operated again, the contact between the delaying member and drive member is released and the delaying member is pushed across the priming stroke length into the second position. The state of the administering device at any instant as the dose is being administered can be marked by the releasable fixed positions so that the positions are perceptible or alternatively audible to the user.

For the purposes of the present invention, a contact is established between the at least one delaying member and the drive member in such a way that when the drive button is operated, the drive member is able to slide in the forward direction. This being the case, contact is established either in the first position of the delaying member before or in the second position, once the delaying member has been displaced relative to the drive member. This means that, as a result of the invention, it is possible to provide a priming stroke either before or after the dose has been administered, thereby lengthening the actuating length of the drive button during administration. Preferably, a priming stroke is effected after the dose has been administered. This ensures that the dose will be reliably dispensed.

In one embodiment, when the drive button is operated, a contact can be established between the delaying member and the plunger rod or drive member by an axial abutment of two abutment edges in the longitudinal direction of the device. This being the case, one abutment edge with a radially extending surface is provided on the delaying member and another abutment edge is provided on the plunger rod, the surface of which moves into contact with the surface of the first abutment edge on establishing contact. It is also possible for a contact to be established between the delaying member and the plunger rod due to a radial engagement of the delaying member in the plunger rod or drive member, for which purpose the plunger rod and the drive member are preferably designed as toothed racks. Also for this purpose, at least one driver is provided on a delaying member, preferably a zigzag projection, which engages in the plunger rod or drive member in a radial direction when the delaying member is in the second position. The driver is preferably provided in the form of a zigzag-shaped projection on the end of the delaying member lying opposite the drive button.

When the drive button of an administering device in accordance with the present invention is operated in the forward direction, a priming stroke length is initially overcome. As the operating button and, hence, also the delaying member, is moved out of the first position into the second position, the plunger does not move, which also means that no product is dispensed. Not until the delaying member in the second position has established contact with the plunger rod or drive member and the drive button has been operated again is the plunger rod with the plunger pushed in the forward direction across a path length defining a dose so that a product dose is forced out of the reservoir. This being the case, it is of advantage if the distance between the first position and the second position along the longitudinal axis of the administering device, i.e., the priming stroke length, is considerably longer than the dose displacement length which has to be overcome by the plunger in order to dispense a dose. In some embodiments, the priming stroke length is preferably several times that of the dose displacement length.

When administering a product using a device in accordance with the present invention, the total length across which a drive button is pushed forward or is pushed into the housing of the device as a result of the priming stroke is made significantly longer than is the case with the prior art. As a result of this extended displacement length, a user is better able to control the force applied when operating the drive button, making it easier to hold and guide the administering device when dispensing the dose. As a result of a continuous transition from the operation to overcome the priming stroke length to overcoming the dose displacement length or vice versa, a fluid product can be injected softly, for example. Especially in the case of doses of small volume, i.e., if the dose displacement lengths are short, the administering process is made easier for the user because an extended displacement path is more readily visible and the first and second position perceptibly indicate the position and state of the device during administration.

The dose displacement length of an administering device may be a constant displacement length for every injection. However, in some embodiments, it is preferable to provide an administering device with a dose metering unit. To this end, a sleeve body may be used as a dose metering element, which is connected to a rear housing part to prevent it from sliding but is rotatable about a common longitudinal axis. Rotating this dose metering unit sets the maximum dose displacement length which the plunger rod is able to travel. The dose metering unit may be a dose metering unit of the design described in patent specification WO 97/36625, in which case it may co-operate with a drive member also of the described type in order to meter doses.

In one embodiment of the present invention, the first and the second position are determined by a guide profile in the interior of the administering device. The guide profile is preferably provided by means of the shape of a surface lying opposite the delaying member and along which the delaying member slides. The guide profile may be provided, for example, on the external face of the plunger rod or also on the internal face of the housing or a dose metering unit, in which case the latter will form a part of the housing. The guide profile might also be distributed over several surfaces, e.g., one profile for a first position on one face and another profile for the second position on another face. The guide profile may naturally also be provided in the form of several individual guide profiles on different faces. The delaying member has at least one projection, which is guided along the guide profile when the drive button is operated. However, it would also be conceivable to provide one or more projections on a face of the plunger rod, drive member, housing or dose metering unit and a guide profile on a surface of the delaying member. The projection is preferably in constant contact with the profiled surface and the surface to be overcome between the first and the second position has a defined friction resistance. The friction resistance may be such that the force needed to effect the displacement between the two positions of the delaying member approximately corresponds to the force necessary to operate the drive button in order to dispense the product. This results in a continuous movement from the point at which operation of the drive button is initiated until the dose has been completely dispensed, in which case the state during the administering process is indicated due to a temporarily higher resistance between the first and second position. In order to create the friction surfaces, the components of the administering device may be manufactured as dual-component injection-moulded parts, which have a hard-soft connection, resulting in friction surfaces of differing resistance.

In a preferred embodiment, the guide profile is provided in the form of a guide track, recessed in the longitudinal direction of an external face or surface of a plunger rod or a drive member. A recess is provided in the guide track for the first position and a second recess is provided for the second position of the delaying member, in which case the first recess is preferably near or at one end of the guide track and the second recess is preferably near or at the other end. Disposed on the surface of the delaying member lying opposite the guide track is a projection, which locates or lodges in the first recess on the surface of the drive member in a first releasable fixed position. When the drive button is operated, the resistance induced by the projection being in the recess is overcome. The resistance is higher if a dose displacement length has to be overcome first, for which purpose the delaying member remains in the first position during the forward movement. If the priming stroke length has to be overcome first, it is lower, which means that the delaying member can be easily released from the first position. Once the resistance has been overcome, the projection is pushed along the recessed guide track until it locates or is received in the second recess in a second releasable fixed position. In this position, contact can be simultaneously established between the operating button and the plunger rod or a drive member connected to the plunger rod. In some embodiments, at another point of the plunger rod or the drive member, an additional guide profile may be provided, which is also provided in the form of a recessed guide track. A step or an offset on the delaying member is able to locate in this guide track and act as an additional guide as the delaying member moves between the two releasable fixed positions. The user is able to feel the projection of the delaying member as it latches in the recesses of the first guide track, giving him feedback about the progress of the administering process.

It is also possible for the second releasable fixed position of the delaying member to be defined by the contact between two abutment edges designed to establish a contact between the delaying member and the plunger rod. A recess for this second releasable fixed position is not absolutely necessary in this case. To this end, a radially extending abutment edge of the delaying member may move into abutment with the end face of the drive member, for example.

In another preferred embodiment, the plunger rod is provided in the form of a toothed rack and the delaying member has at least one driver in the form of a claw, which can engage in a row of teeth of the toothed rack. The delaying member is mounted on a drive button in a web shape in the extension thereof so that it does not engage in the row of teeth initially. A step-shaped guide profile or a dose metering element is provided on an internal face of the housing lying opposite the delaying member. The steps rise radially towards the interior in the forward direction. On a side facing this internal face, the delaying member has a projection which lies in abutment with the profiled surface. The delaying member is initially pushed by means of the drive button along a first surface in the forward direction along the guide profile, corresponding to the priming stroke length, until it reaches a first step of the guide profile. The projection overcomes this first step as the displacement of the drive button continues, causing the delaying member to be bent radially in the direction of the toothed rack. The step surface is preferably disposed at an angle relative to the longitudinal axis of the device in order to make it easier to overcome the step. As the step is overcome, the claw of the delaying member locates in the row of teeth of the toothed rack and comes into contact with a tooth flank of the row of teeth, thereby establishing the contact proposed by the invention. In this position, the delaying member is disposed in the second position relative to the toothed rack.

As the displacement of the drive button continues, the projection of the delaying member is guided along a second surface in the guide profile adjoining the first step. As this happens, the delaying member is engaged with the plunger rod or drive member and therefore pushes it in the forward direction so that product is forced out of the reservoir. This second surface in the guide profile preferably corresponds to the dose displacement length for administering the product. Once this surface has been overcome, the projection preferably moves into abutment with a second step of the guide profile, at which point the dose ceases to be administered. The second step may also be provided in the form of a stop, which may be adjusted in the forward direction by means of a dose metering unit. In addition, it may be of advantage if the delaying member moves into abutment with its end face against an inwardly directed edge of the housing, which may serve as an additional feature to prevent any further movement of the plunger rod.

As the drive button is pulled back for a subsequent administration process, a return lock in the form of a locking means which engages in the row of teeth of the toothed rack also prevents the toothed rack from being retracted as well. The drivers or claws of the delaying member are pulled back across the flat flanks of the row of teeth and, because of its elasticity, the delaying member bends initially, due, in some embodiments, to its web-shaped design, until the projection on the guide profile has overcome the first step radially outwards, so that the delaying member is no longer located between the teeth of the row of teeth. The delaying member or the drive button are pulled back far enough for the delaying member to move back into its first position against a rearward third step of the guide profile. The administering device is then ready for administering again. With every administering process, the toothed rack is preferably pushed farther in the forward direction by a tooth distance corresponding to the dose displacement length. With this embodiment, it is not absolutely necessary to provide a dose metering unit.

In yet another embodiment of the present invention, it is possible to provide several delaying members, which are telescopically guided one inside the other and respectively have a first and a second releasable fixed position relative to one another and to the plunger rod. When the drive button is displaced, one of the delaying members is firstly moved out of its first position into its second position and as the displacement of the drive button continues, a second delaying member is then moved out of its first position into its second position. As soon as the last delaying member has reached its second position, the contact with the plunger rod or with a drive member for the plunger rod is established so that a dose can be administered.

BRIEF DESCRIPTION OF THE DRAWINGS

FIG. 3 is a cross-section in the longitudinal direction through an administering device with a delaying member in a first position, representing another embodiment of the invention, FIG. 4 is a cross-section similar to that shown in FIG. 3, but with the delaying member located in a toothed rack, FIG. 7 is a cross-section through a part of the administering device with the drive mechanism in a released state when the drive button is pushed in.

DETAILED DESCRIPTION OF THE DRAWINGS

Figure 1:
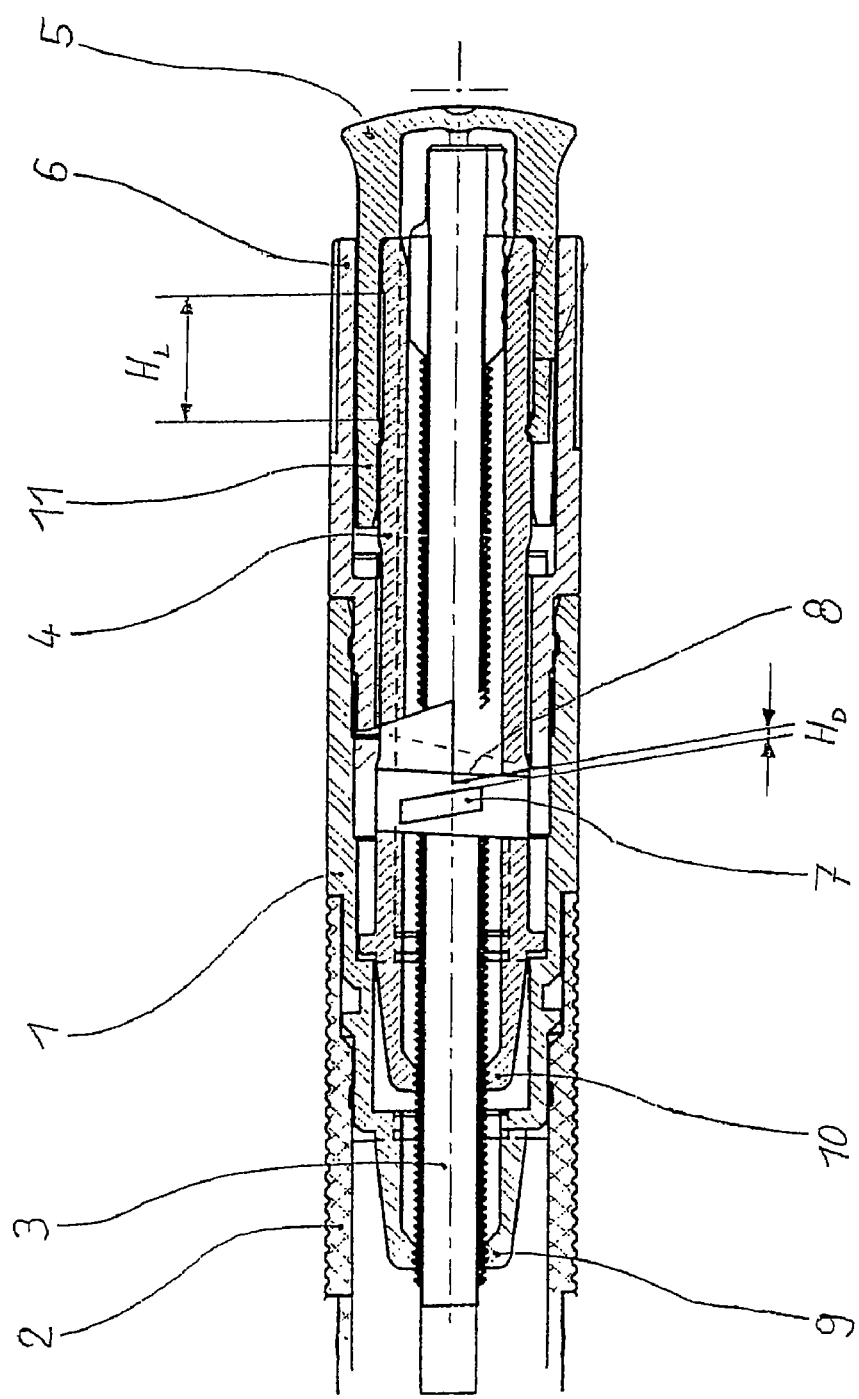
FIG. 1 is a cross-section in the longitudinal direction through a part of an administering device with a drive unit and a delaying member, representing an embodiment of the present invention.

FIG. 1 illustrates a drive mechanism in a region of an administering device in the form of an injection pen. The injection pen has a housing comprising a housing sleeve 1 in the region where the drive mechanism is disposed and a housing sleeve 2 in a region which adjoins the administering mechanism and accommodates an ampoule (not illustrated, but of the known types) with an injectable product constituting a product reservoir. The product is a fluid product, e.g. an active substance in solution such as insulin. A plunger is accommodated in the ampoule, which when pushed in the forward direction forces the product out of the ampoule through an ampoule outlet and dispenses it via an injection needle. The plunger is moved in the forward direction in the ampoule by means of the drive mechanism, comprising a toothed rack 3 as the plunger rod acting directly on the plunger, and a drive member 4. The drive member 4 is mounted so as to be slidable in the forward direction of the plunger and in the opposite direction. A drive button 5 projects towards the rear out of the injection pen at an end lying opposite the outlet.

The injection pen illustrated in FIG. 1 is also equipped with a dose metering unit. To this end, it has a dose metering element 6 in the form of a sleeve body, which is secured to the housing sleeve 1 so that it is unable to slide and connected to it so as to be rotatable about the common longitudinal axis. When the metering element 6 is rotated, the dose displacement length in the forward direction of the drive member 4 and the toothed rack 3 needed to dispense a dose of a specific volume is set. For metering purposes, the dose metering element 6 is turned relative to the housing sleeve 1, so that a distance $H_D$ corresponding to a dose displacement length results between a collar 7 standing proud of an external surface of the drive member 4 and a spirally extending end face 8 of the dose metering element 6 lying opposite the collar 7.

The drive member 4 can be pulled back relative to the housing sleeve 1 and hence also relative to the plunger in the ampoule in the direction opposite the forward direction by the dose displacement length. When the drive member 4 is pulled back, the toothed rack 3 remains in the position which it assumed relative to the housing during the dose metering process. It is prevented from sliding in the direction opposite the forward direction by locking means 9 disposed on the housing sleeve 1. In the embodiment illustrated here, the locking means 9 are provided in the form of latch cams, each in the form of an elastic tongue projecting out from a front end of the housing sleeve 1 and extending radially inwards towards the toothed rack 3. The locking means 9 co-operate in such a way with a row of teeth of the toothed rack 3 directed towards them that they enable the toothed rack 3 to slide in the forward direction and prevent a movement in the direction opposite the forward movement by engaging in a positive lock.

The toothed rack 3 is moved in the forward direction by means of the drive member 4. To this end, the drive member has tongues in the forward direction, which have drivers 10 projecting radially inwards at their front ends. When the drive member 4 moves in the forward direction, one of the drivers 10 locates in a row of teeth of the toothed rack 3 facing it, forcibly driving the toothed rack 3 with it in the forward direction. The tongues of the drive member 4 incorporating the drivers 10 are of an elastic design so that when the drive member 4 is moved in the direction opposite the forward direction, the drivers slide across the rows of teeth of the toothed rack 3, which is blocked by the locking means 9.

FIG. 1 illustrates a delaying member 11 proposed by the invention, which is provided as an integral part of the drive button 5. Naturally, it would also be conceivable for the delaying member 11 and drive button 5 to be provided as separate components in a fixed connection. In the embodiment illustrated, the delaying member 11 is provided as an extension of the drive button 5. The extension preferably consists of one or more webs 12, 13. However, it may also be provided in the form of a sleeve. The delaying member 11 is disposed in the radial direction between the drive member 4 and the dose metering element 6. If the injection pen does not have a dose metering unit, the delaying member 11 may be provided between the drive member 4 and a housing sleeve 1, for example. An injection pen without a separate drive member would also be conceivable, in which case the delaying member 11 would be disposed between the plunger rod or toothed rack and a housing sleeve.

Figure 2:
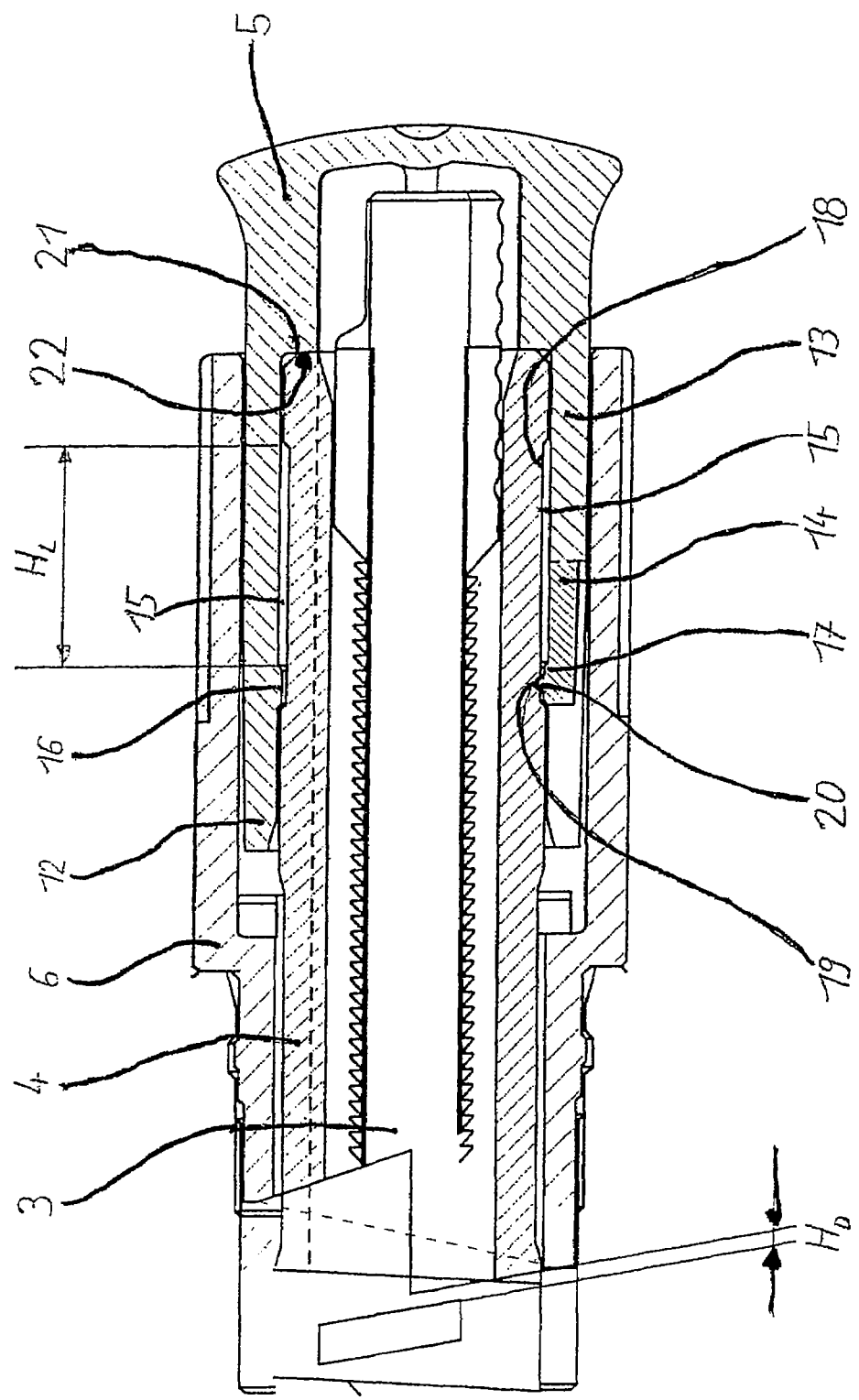
FIG. 2 is a cross-section through the part of the administering device incorporating the delaying member of FIG. 1, but on an enlarged scale.

The region of the injection pen incorporating the delaying member 11 is illustrated on a larger scale in FIG. 2. The delaying member 11 has a web 12 and a web 13 lying opposite it. The web 13 has an extension 14 on its end face, which has a higher flexibility or bending capacity than the web 13. On the external surface of the drive member 4, guide tracks 15 are recessed into the surfaces lying opposite the webs 12 and 13, which extend in the longitudinal direction of the injection pen. On the surfaces of the web 12 and the extension 14 pointing radially inwards, a step 16 is respectively provided for the web 12 and a step 17 for the extension 14. The steps are designed to be high enough to locate in the guide tracks 15 whilst still permitting the external surface of the drive member 4 and the internal face of the webs 12 and 13 to sit in abutment with one another. Accordingly, the edges of the steps 16 and 17 move into abutment with the respective oppositely lying edges of the guide tracks 15. The delaying member 11 is therefore mounted so as to be essentially slidable along the length of the guide tracks 15 relative to the drive member.

In the guide track 15 for the extension 14, a first recess 18 is provided in a region close to the drive button 5 for a first releasable fixed position of the delaying member 11. In a region of the guide track 15 at a distance from the drive button 5, a second recess 19 is provided for a second releasable fixed position of the delaying member 11. A cam 20 projects out from the step 17 of the extension 14 in the direction towards the recesses 18 and 19. The extension 14 is flexibly biassed so that the cam 20 projects into the recesses 18 and 19 when it lies opposite them. In a position between the recesses 18 and 19, the extension 14 is bent back by the height of the recesses so that the extension 14 slides along the guide track as the delaying member 11 is moved relative to the drive member 4. As a result of the cam 20 latching in the first and the second recesses 18 and 19, a user is able to feel and hear when the delaying member 11 assumes the first and the second releasable fixed position relative to the drive member 4.

As the delaying member 11 slides across the length of the guide track 15, the toothed rack 3 remains stationary relative to the housing sleeve 1 and dose metering element 6. When the drive button 5 and hence the delaying member 11 is displaced between the first releasable fixed position 18 and the second releasable fixed position 19, the plunger is therefore not moved in the ampoule or reservoir and no product is forced out of the reservoir. The distance between the first and the second recess 18 and 19 and the length of the guide track therefore constitute a priming stroke length $H_L$ for the administering device.

When the cam 20 perceptibly latches in the second recess 19, i.e. the delaying member 11 is in its second releasable fixed position, an end face 21 of the drive button 5 moves into abutment with an end face 22 of the drive member 4 lying opposite it and establishes a contact between the delaying member 11 and the drive member 4. The end faces therefore serve as abutment edges for establishing the contact. The end face 21 of the drive button 5 may be regarded as a step of the delaying member 11 projecting radially inwards and thus forms a transition between the delaying member 11 and the drive button 5. When the drive button 5 is moved from this second position farther along in the forward direction, the drive member 4 is pushed in the forward direction relative to the housing sleeve 1 due to the contact. The drive button 5 can be pushed in the forward direction until the dose displacement length $H_D$ illustrated in FIG. 1 has been overcome and the drive member 4 sits against an abutment edge on the housing sleeve 1.

In its fully extracted position, the drive button 5 is disposed in the first releasable fixed position, i.e. the cam 20 projects into the first recess 18. When the drive button is moved in the forward direction, the cam 20 can be released from the recess 18 and the steps 16 and 17 slide in their respective guide tracks 15 across the priming stroke length $H_L$ until the cam 20 locates in the second recess 19 so that the delaying member 11 is in its second releasable fixed position. In this second position, contact is established between the delaying member 11 or drive button 5 and the drive member 4 due to the abutment of the end face 21 of the drive button 5 with the end face 22 of the drive member 4. The continued movement of the drive button in the forward direction causes the drive member 4 to move relative to the housing sleeve 1 until the dose displacement length $H_D$ has been overcome. As may also be seen from FIG. 1, the priming stroke length $H_L$ is significantly longer than the dose displacement path $H_D$. This enables the user to administer the product more sensitively and more safely if injecting a small dose quantity, i.e. by an injection having only a short dose displacement length $H_D$.

Alternatively, it would be possible to make the resistance afforded to the cam 20 as it moves out of the first recess 18 so high that when the drive button 5 is operated, the toothed rack 3 is moved first until the end face 8 abuts with the collar 7, so that the dose displacement length $H_D$ has been covered. Only then is the resistance overcome and the priming stroke length $H_L$ covered.

If the delaying member 11 is sleeve-shaped and extends around the drive member 4, the guide tracks may be provided in the form of an annular region of the drive member 4 with a widened internal circumference. This being the case, both the first recess 18 and the second recess 19 may be provided in the form of annular recesses. In order to define the resistance, the width of the cam may be varied. It would also be possible to provide several cams.

In order to prepare for an administering procedure, the drive button 5 is moved in the direction opposite the forward direction into a position in which it is extracted from the injection pen. Accordingly, the delaying member 11 is firstly moved back from the second position into the first position and, as the drive button 5 is pulled further out, the drive member 4 is then pulled back relative to the housing sleeve 1 in the direction opposite the forward direction. As the drive member 4 is pulled back, the drivers 10 on the tongues of the drive member 4 are pulled back across the row of teeth of the toothed rack 3. A new dose may now be set with the dose metering element 6, so that the injection pen is ready to administer injectable product again.

FIGS. 3 to 9 illustrate a second embodiment of an administering device in accordance with the present invention. FIG. 3 illustrates an injection pen with a housing sleeve 1, the front end of which accommodates an ampoule 23 and the rear end of which accommodates a drive mechanism. At the front part of the ampoule 23, a chamber 24 is provided for an injectable product and opens into an outlet 25. The rear region of the ampoule accommodates a plunger 26 with a connection to a plunger rod 3 provided in the form of a toothed rack. The embodiment of the injection pen illustrated also has a mixing mechanism 27, by means of which a dual-component product can be mixed immediately before being administered.

The drive mechanism in the rear part of the housing sleeve 1 comprises a drive button 5, the toothed rack 3 and a delaying member 11. The drive button 5 and the delaying member 11 are separate components which are fixedly joined to one another. However, they may also be provided as an integral component in this embodiment. The delaying member 11 is an elongate web which is mounted on the drive button 5 by its rear end, whilst its front end has a claw 28 pointing radially inwards. In a middle region, the delaying member 11 has a projection 29 pointing radially outwards. Another housing sleeve 30 is inserted in the housing sleeve 1 and co-operates with the housing sleeve 1.

When the injection pen is in the state illustrated in FIG. 3, the drive button 5 is disposed in a rear stop and the delaying member 11 is disposed in a first position. In this first position, the projection 29 of the delaying member 11 abuts with a step 31 of the housing sleeve 30 pointing radially inwards. In order to assume a releasable fixed position, a surface 32 in the region in front of the step 31 has an additional indentation into which the projection 29 moves due to its bending elasticity. The claw 28 of the delaying member 11 is disposed opposite a row of teeth of the toothed rack 3. When the delaying member 11 is in the first releasable fixed position, the claw 28 is disengaged from the row of teeth.

On the internal face of the housing comprising the housing sleeve 1 and the housing sleeve 30 is a step-shaped guide profile, the steps of which rise radially inwards in the forward direction of the plunger 26 towards the outlet 25. The guide profile may be provided in the form of step-shaped guide ridges or step-shaped recessed annular regions in the internal face of the housing, extending in the longitudinal direction. The guide profile has a surface 32 and a surface 33, and the surface 32 extending from the internal face of the housing is recessed deeper in the housing than the surface 33. The guide profile additionally has a step 31 in the rear region of the surface 32, a step 35 between the surface 32 and the surface 33 and a step 36 in the front region of the surface 33.

Disposed on the internal face of the housing sleeve 1 are tongues 37 which are inwardly inclined in the direction towards the outlet 25. The tongues 37 engage between the teeth of the row of teeth of the toothed rack 3, preventing the toothed rack from moving in the direction opposite the forward direction, and, being flexible, are bent radially outwards when there is a movement in the forward direction so that they slide over the inclined flanks of the row of teeth.

When the injection pen is in the state illustrated in FIG. 4, the drive button 5 together with the delaying member 11 has been pushed in the forward direction towards the outlet 25. As this happens, the projection 29 slides along the surface 32 of the guide profile from the first releasable fixed position, out of the indentation in front of the step 31, into a front region of the surface 32 until it sits in abutment with the step 35. By overcoming the indentation, the delaying member 11 is bent radially inwards to a slight degree and is thus biassed. The stop of the projection 29 on the step 35 constitutes a second position for the delaying member 11. An indentation may also be provided in the surface 32 in front of the edge 35. As it overcomes the indentation for the first position of the delaying member 11, the claw 28 of the delaying member 11 is moved slightly in the direction towards the toothed rack 3 but does not locate in the intermediate spaces of the row of teeth.

When the delaying member moves in the forward direction from the first position into the second position, it moves relative to the toothed rack 3 serving as the plunger rod and relative to the housing sleeve 1. The toothed rack 3 and hence the plunger 26 therefore remain stationary relative to the housing sleeve 1 and no product is forced out of the chamber 24. The movement of the drive button 5 and the delaying member 11 in the forward direction along the surface 32 therefore constitutes a priming stroke. The priming stroke length $H_L$ corresponds to the length of the surface 32 in the longitudinal direction from step 31 to step 35. In the embodiment illustrated, the priming stroke length $H_L$ is 6.8 mm, for example.

Figure 5:
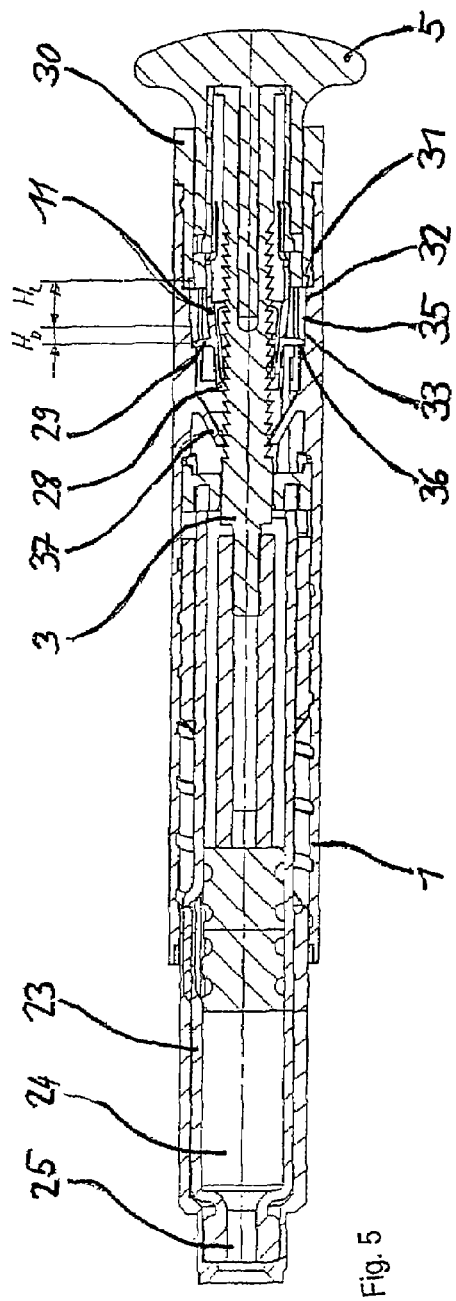
FIG. 5 is a cross-section similar to that shown in FIG. 3, but with the delaying member in a second position.

When the injection pen is in the state illustrated in FIG. 5, the drive button 5 and hence the delaying member 11 have been pushed farther in the direction towards the outlet 25. With this forward movement, the projection 29 of the delaying member 11 overcomes the step 35 in the second position, which is inclined slightly inwards in the forward direction for this purpose. Consequently, the delaying member 11 moves into contact with the toothed rack 3 as the claw 28 is moved so that it lies between the teeth of the row of teeth of the toothed rack 3 and its end face abuts with a vertically extending tooth flank of a tooth of the row of teeth opposite it.

With the continued displacement of the drive button 5, the projection 29 is pushed along the surface 33 of the guide profile as far as the stop on the step 36. Due to the claw 28 locating in the toothed rack 3, the latter is driven in the forward direction so that the plunger 26 is moved towards the outlet 25 and the product is forced out of the chamber 24. With this forward movement, the tongue 37 of the housing sleeve 1 is shifted across the rising flank of a tooth of the row of teeth of the toothed rack 3 from one intermediate space into the subsequent intermediate space. It positively locates in this subsequent intermediate space again, preventing the toothed rack from moving in the direction opposite the forward direction. The length of the surface 33 from the second position against the step 35 to the point where the projection 29 abuts with the step 36 therefore corresponds to a dose displacement length $H_D$, which, in the embodiment illustrated as an example here, is 1.22 mm. This distance also corresponds to the intermediate spaces and teeth of the row of teeth of the toothed rack 3. When a dose is being administered, the tongue 37 therefore migrates on the row of teeth of the toothed rack by one tooth, causing the toothed rack 3 to be moved relative to the housing sleeve 1. A front end face of the drive button 5 may simultaneously be moved against a stop on the housing, which lies outside the section shown in FIG. 5 and is therefore not illustrated.

Figure 6:
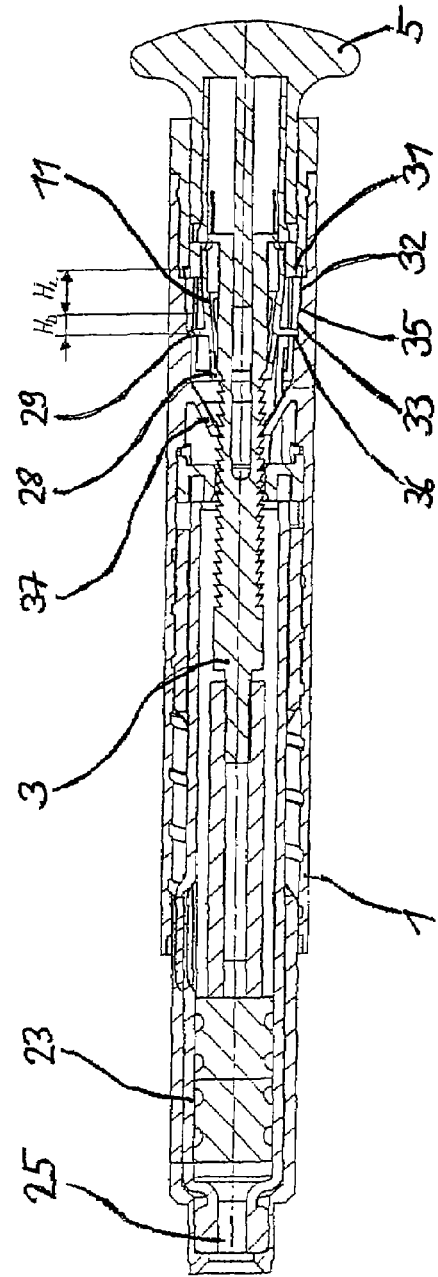
FIG. 6 is a cross-section through an administering device of the type illustrated in FIG. 3 after the last dose has been administered.

FIG. 6 illustrates the injection pen after it has administered several dose units, in which case the plunger 26 is in a front position inside the ampoule 23 and the tongues 37 of the housing sleeve 1 have overcome several teeth of the row of teeth of the toothed rack 3. The delaying member 11 and the drive button 5 are in an engaged position, similar to that illustrated in FIG. 5.

Figure 7:
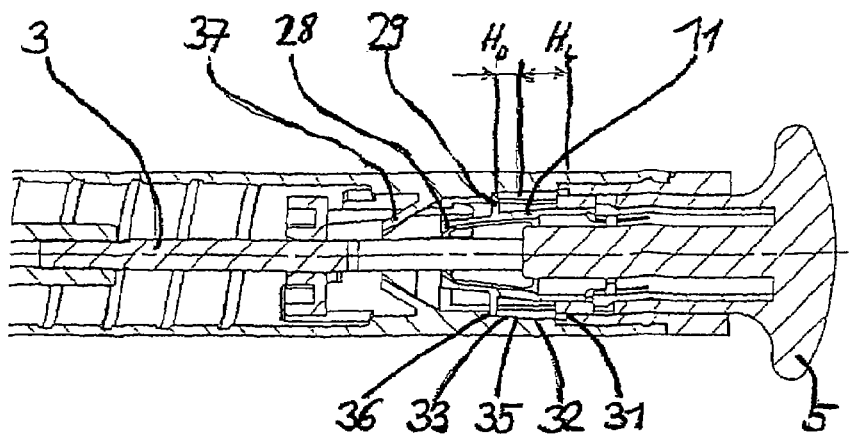

In some cases, it is now necessary to fit a new ampoule 23 in the injection pen and re-set the drive mechanism to an initial position. To do this, the toothed rack 3 must be pulled back in the direction opposite the forward direction. As illustrated in FIG. 7, the drive button may be turned in the circumferential direction of the injection pen for this purpose, as a result of which it drives with it and also rotates the toothed rack 3. As a result of this rotation, the tongues 37 and the claws 28 are disengaged from the toothed rack 3 because the row of teeth turns with the toothed rack 3 and there are no teeth opposite the tongues 37 and claws 28 when the toothed rack 3 is in this turned position. The toothed rack 3 is therefore in a released position.

Figure 8:
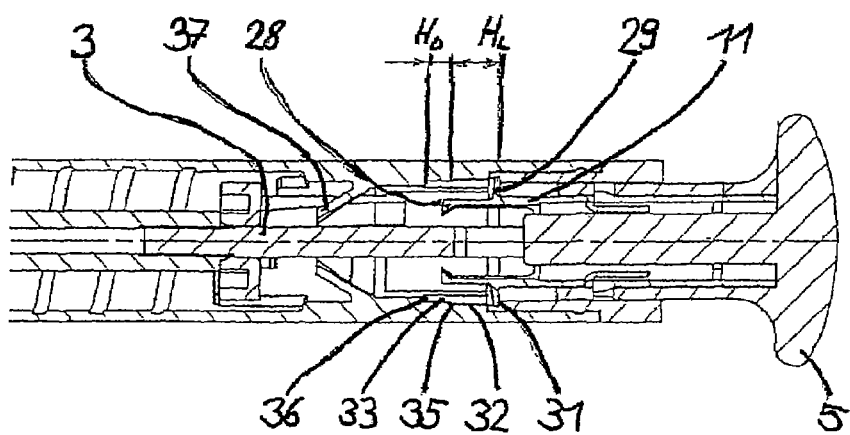
FIG. 8 is a cross-section similar to that shown in FIG. 7, but with a retracted drive button.
Figure 9:
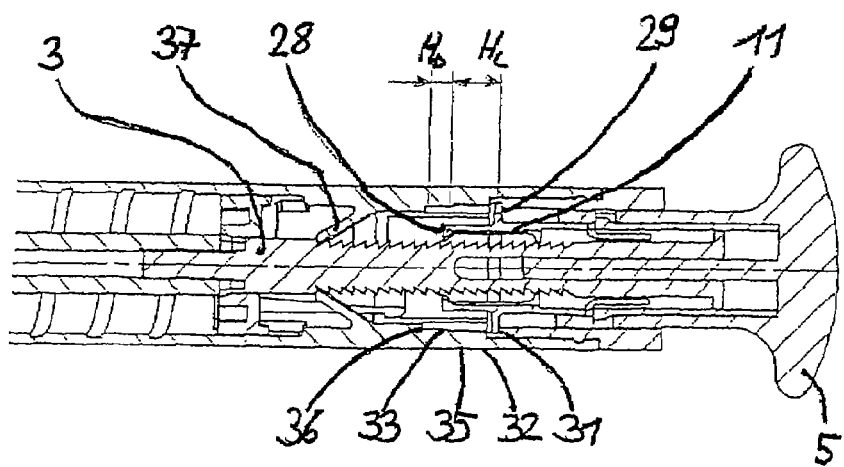
FIG. 9 is a cross-section similar to that shown in FIG. 7, but with a retracted toothed rack in a locked state.

In FIG. 8, the drive button 5 and the delaying member 11 have been pulled back as far as the stop on the step 31 with the delaying member 11 in a first releasable fixed position. When released, the toothed rack 3 may be returned to its rear position, for example by means of a biasing element between the toothed rack 3 and, for example, the housing sleeve 1, which is biased as a result of the forward movement of the toothed rack 3 in the forward direction.

When the toothed rack is in the rear position, the drive button 5 and hence the toothed rack 3 are turned back into the original position, so that the tongues 37 engage with the rows of teeth of the toothed rack 3. The drive unit of the injection pen is therefore in an initial position in which the tongues 37 are moved so that they sit positively in the first gap of the row of teeth of the toothed rack 3. A new ampoule 23 can now be inserted in the front region of the housing sleeve 1. The injection pen is now ready for administering an injectable product again.

The injection pen of the embodiment illustrated in FIGS. 3 to 9 does not have a separate dose metering unit. The dose is determined by the dose displacement length $L_D$, i.e., the length of the step 33, or distance between the teeth of the row of teeth of the toothed rack 3 and corresponds to a priming function. However, it would also be conceivable to provide a separate dose metering unit for an injection pen with a stepped guide profile, of the type described with respect to the embodiment illustrated in FIGS. 1 and 2, for example.

When the drive button 5 is operated by a user, the delaying member 11 is moved from its first releasable fixed position against the step 31 to a second position against the step 35 along the priming stroke length $H_L$. The first and the second position of the delaying member are therefore spaced apart from one another in the guide profile so that the priming stroke length $H_L$ is significantly longer than a dose displacement length $H_D$. In the embodiment illustrated in FIGS. 3 to 9, the priming stroke length $L_H$ is several times longer than the dose displacement length $H_D$. As the displacement of the drive button 5 continues, the delaying member 11 moves into contact with the toothed rack 3 in the second position so that the dose displacement length $H_D$ is overcome by the drive button 5 and the toothed rack is moved in the forward direction.

The total length which the drive button 5 overcomes is therefore made up of the priming stroke length $H_L$ and the dose displacement length $H_D$. This extended administering movement of the drive button 5 makes it easier for a user to follow the progress of the injection and ensure that the product is administered reliably. When the tongue 37 overcomes a tooth of the row of teeth of the toothed rack 3 when a dose is being administered, a clicking noise occurs as the tongue 37 makes contact with the flank of a subsequent tooth. The user is therefore audibly aware of the product dose being administered. Due to the indentations in the guide profile, he is able to feel the state of the injection pen as the drive button 5 is displaced because it is necessary to vary the pressure slightly at the different positions of the guide profile. In order to define the requisite pressure and enable the drive button 5 and hence the delaying member 11 to be displaced continuously, the surfaces 32 and 33 of the guide profile may be provided in the form of friction surfaces, by means of which a desired friction resistance is exerted on the projection 29 during the displacement. The flexibility of the delaying member 11, i.e., its bending stiffness, may also be selected so that a desired displacement pattern is obtained during the administering process. In the embodiment illustrated in FIGS. 3 to 9, the delaying member 11 simultaneously serves as a drive member for administering the product.

The present invention is described with reference to two exemplary embodiments. However, other constructions of devices for administering doses of a product would also be conceivable without departing from the scope of the present invention. In particular, it would be possible to use any suitable housing parts, drive members, delaying members, plunger rod elements and different locking mechanisms, as along as a delay element is moved from a first position into a second position relative to the plunger rod along a priming stroke length $H_L$ while the plunger rod remains stationary relative to the housing, and the delaying member comes into contact with the plunger rod in the second position so that the continued displacement of the drive button causes the plunger rod to move relative to the housing across a dose displacement length $H_D$ in order to administer the injectable product.

Embodiments of the present invention, including preferred embodiments, have been presented for the purpose of illustration and description. They are not intended to be exhaustive or to limit the invention to the precise forms and steps disclosed. Modifications or variations are possible in light of the teachings herein, and all such modifications and variations are within the scope of the invention as determined by the appended claims when interpreted in accordance with the breadth to which they are fairly, legally, and equitably entitled.

The invention claimed is:

1. A device for administering metered doses of an injectable product, comprising:
   a) a housing incorporating a reservoir for the product,
   b) at least one drive member with a plunger which forces product out of the reservoir through an outlet when moved in a forward direction,
   c) a drive button which, when displaced, moves the drive member relative to the housing, and
   d) at least one delaying member moveable from a first position into a second position at a distance apart from the first position by displacing the drive button relative to the drive member in the longitudinal direction of the device, wherein the first position and the second position of the delaying member are defined by a guide profile in the form of a guide track recessed into the delaying member or the external face of the drive member and having a first recess for the first position of the delaying member and a second recess for the second position of the delaying member, whereby the drive member remains stationary relative to the housing during movement of the delaying member from the first position into the second position and the at least one delaying member establishes contact with the drive member in the first or second position so that when the drive button is displaced, the drive member is moveable in the forward direction before or after the at least one delaying member is moved relative to the drive member.

2. The administering device as claimed in claim 1, wherein the first position and the second position of the delaying member are releasable fixed positions.

3. The administering device as claimed in claim 1, wherein the distance between the first position and the second position of the delaying member along the longitudinal axis of the device constitutes a priming stroke length which is several times longer than the dose displacement length traveled by the drive member in the forward direction order to administer a product dose.

4. The administering device as claimed in claim 1, wherein the delaying member has at least one projection which is guided along the guide profile.

5. The administering device as claimed in claim 1, wherein the contact between the delaying member and the drive member is established by means of an abutment edge on the delaying member coming into contact in the longitudinal direction of the device with an on opposing abutment edge on the drive member.

6. The administering device as claimed in claim 1, wherein the contact between the delaying member and the drive member is established by at least one driver of the delaying member engaging in the drive member.

7. The administering device as claimed in claim 1, wherein at least two delaying members are telescopically slidable relative to one another when the drive button is displaced in the longitudinal direction of the device.

8. The administering device as claimed in claim 1, further comprising at least one friction surface between the delaying member and the housing or the drive member, said friction surface having a defined friction resistance.

9. A device for administering metered doses of an injectable product, comprising:
  a) a housing incorporating a reservoir for the product,
  b) a drive member with a plunger which forces product out of the reservoir through an outlet when the plunger is moved in a forward direction,
  c) a drive button which, when displaced, moves the drive member relative to the housing, and
  d) a delaying member moveable from a first position to a second position at a distance apart from the first position by displacing the drive button relative to the drive member in the longitudinal direction of the device, wherein the first position and the second position of the delaying member are defined by a guide profile disposed on one of the delaying member, the external face of the drive member or on the housing opposite the delaying member, and wherein the guide profile comprises a recess for the first position and an abutment edge on an end face of the drive member for the second position, which is opposite an abutment edge of the drive button or the delaying member, whereby the drive member remains stationary relative to the housing during movement of the delaying member from the first position to the second position and the delaying member establishes contact with the drive member in the first or second position so that when the drive button is displaced, the drive member is moveable in the forward direction before or after the delaying member is moved relative to the drive member.

10. The administering device as claimed in claim 9, wherein the first position and the second position of the delaying member are releasable fixed positions.

11. The administering device as claimed in claim 9, wherein the distance between the first position and the second position of the delaying member along the longitudinal axis of the device constitutes a priming stroke length which is several times longer than the dose displacement length traveled by the drive member in the forward direction to administer a product dose.

12. The administering device as claimed in claim 9, wherein the delaying member has at least one projection which is guided along the guide profile.

13. The administering device as claimed in claim 9, wherein the contact between the delaying member and the drive member is established by an abutment edge on the delaying member coming into contact in the longitudinal direction of the device with an opposing abutment edge on the drive member.

14. The administering device as claimed in claim 9, wherein the contact between the delaying member and the drive member is established by at least one driver of the delaying member engaging in the drive member.

15. The administering device as claimed in claim 9, comprising at least two delaying members telescopically slidable relative to one another when the drive button is displaced in the longitudinal direction of the device.

16. The administering device as claimed in claim 9, further comprising at least one friction surface between the delaying member and the housing or the drive member, said friction surface having a defined friction resistance.

* * * * *

UNITED STATES PATENT AND TRADEMARK OFFICE
CERTIFICATE OF CORRECTION

PATENT NO. : 7,699,816 B2 Page 1 of 1
APPLICATION NO. : 11/106024
DATED : April 20, 2010
INVENTOR(S) : Fritz Kirchhofer It is certified that error appears in the above-identified patent and that said Letters Patent is hereby corrected as shown below:

SPECIFICATION

| Column | Line | PTO | Should Read |
|---|---|---|---|
| 13 | 50 | "dose displacement length $H_D$ As the" | -- dose displacement length $H_D$. As the -- |

CLAIMS

| Column | Line | PTO | Should Read |
|---|---|---|---|
| 15 | 18 | "device with an on opposing" | -- device with an opposing -- |

Signed and Sealed this

Thirteenth Day of July, 2010

David J. Kappos
*Director of the United States Patent and Trademark Office*